US012343431B2

(12) United States Patent
Carson et al.

(10) Patent No.: US 12,343,431 B2
(45) Date of Patent: Jul. 1, 2025

(54) LYOPHILIZED AND STABILIZED LIVE ATTENUATED FORMULATED VACCINE AGAINST TULAREMIA

(71) Applicant: Southwest Research Institute, San Antonio, TX (US)

(72) Inventors: Kenneth H. Carson, San Antonio, TX (US); Spring M. Cabiness, Mico, TX (US); Amy M. De Los Santos, San Antonio, TX (US); Karl Klose, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 18/503,901

(22) Filed: Nov. 7, 2023

(65) Prior Publication Data

US 2024/0148654 A1   May 9, 2024

Related U.S. Application Data

(60) Provisional application No. 63/382,667, filed on Nov. 7, 2022.

(51) Int. Cl.
*A61K 9/19*     (2006.01)
*A61K 39/00*    (2006.01)
(Continued)

(52) U.S. Cl.
CPC ............ *A61K 9/19* (2013.01); *A61K 39/0208* (2013.01); *A61P 37/04* (2018.01);
(Continued)

(58) Field of Classification Search
CPC ....... A61K 9/19; A61K 39/0208; A61P 37/04; Y02A 50/30
See application file for complete search history.

(56) References Cited

U.S. PATENT DOCUMENTS

| 11,738,075 B2* | 8/2023 | Conlan | A61K 9/0019 |
| | | | 424/246.1 |
| 2013/0072881 A1 | 3/2013 | Khandke et al. | |

(Continued)

FOREIGN PATENT DOCUMENTS

| WO | WO-2014029758 A1 * | 2/2014 | ............ A23C 9/12 |
| WO | 2019/138210 | 7/2019 | |
| WO | 2021/163490 | 8/2021 | |

OTHER PUBLICATIONS

Pansare and Patel. (2019). "Lyophilization Process Design and Development: A Single-Step Drying Approach." J Pharm Sci, 108(4):1423-1433. (Year: 2019).*

(Continued)

*Primary Examiner* — Gary B Nickol
*Assistant Examiner* — Bailey M Morgan
(74) *Attorney, Agent, or Firm* — Grossman, Tucker, Perreault & Pfleger, PLLC (57) ABSTRACT

A lyophilized stabilized formulation containing a live attenuated vaccine strain against tularemia. The method includes supplying the immunogenic agent comprising Fn-igIDOAg$^{FTT}$ and subjecting the immunogenic agent to lyophilization and recovering a lyophilized and stabilized form of such immunogenic agent.

1 Claim, 14 Drawing Sheets

(51) Int. Cl.
    *A61K 39/02* (2006.01)
    *A61P 37/04* (2006.01)
(52) U.S. Cl.
    CPC .... *A61K 2039/522* (2013.01); *A61K 2039/54* (2013.01); *Y02A 50/30* (2018.01)

(56) References Cited

U.S. PATENT DOCUMENTS

| | | |
|---|---|---|
| 2019/0070282 A1 | 3/2019 | Watson et al. |
| 2020/0261369 A1* | 8/2020 | Fela .................. A61K 9/19 |
| 2021/0170019 A1 | 6/2021 | Cui et al. |

OTHER PUBLICATIONS

Invitation to Pay Additional Fees from related PCT Appln. No. PCT/US2023/078971, dated Feb. 13, 2024.
Zogaj et al., "Engineering OAgFTT expression in F. novicida", 9th International Conference on Tularemia, Oct. 2013, Canada, pp. 1-3.
Chu et al., "Live Attenuated Francisella novicida Vaccine Protects against Francisella tularenis Pulmonary Challenge in Rats and Non-human Primates", PLOS Pathogens, vol. 10, Issue 10, Oct. 2014, U.S., pp. 1-10.
Farlow et al., "Francisella tularensis in the United States", Emergin Infectious Diseases, vol. 11, No. 12, Dec. 2004, Arizona, U.S., pp. 1835-1841.
International Search Report and Written Opinion from related PCT Appln. No. PCT/US2023/078971, dated Apr. 23, 2024.

* cited by examiner

LYOPHILIZED AND STABILIZED LIVE ATTENUATED FORMULATED VACCINE AGAINST TULAREMIA

GOVERNMENT SUPPORT

This invention was made with U.S. Government support under Agreement No. W15QKN-16-0-1002 awarded by the ACC-NJ to the MCDC. The Government has certain rights in the invention.

FIELD

The present invention is directed at a lyophilized stabilized formulation containing a live attenuated vaccine strain against tularemia.

BACKGROUND

Tularemia is caused by the gram-negative intracellular pathogen *Francisella tularensis*. This bacterium was first identified in 1912. *Francisella tularensis* is currently listed as a category A selected agent. Since the discovery of this pathogen, at least four (4) subspecies have been identified that exhibit distinct virulence and biochemical profiles. Human disease is primarily associated with two *F. tularensis* subspecies: the highly virulent *F. tularensis* subsp. *tularensis* (Ftt) which is found in North America and the moderately virulent *F. tularensis* subsp. *holarctica* which is endemic throughout the Northern Hemisphere. See, e.g., *Francisella tularensis* in the United States, Farlow et al, Emerging Infectious Diseases, Vol. 11, No. 12 (December 2005).

Currently, the only vaccine used to treat tularemia caused by *Francisella tularensis* is the Live Vaccine Strain (LVS), an attenuated type B (*F. tularensis* subsp. *holarctica*) strain that does not appear to cause in humans but has unknown genetic stability and safety which makes it a poor candidate for FDA approval. As such, *F. tularensis* is classified as a category A select agent and is a threat to the general public as well as the warfighter.

Other relatively more recent efforts have reported on the use of an engineered form of *Francisella novicida* (Fn) in the form of Fn-igiD OAg$^{FTT}$ as a candidate for a tularemia vaccine. See, e.g., Engineered OAg$^{FTT}$ expression *F. novicida*, X. Zogay, A. Adelani, J. Nguyen, P. Chu, K. Klose, 9$^{th}$ International Conference on Tuleremia, October 2018.

A need remains to produce an FDA-approved formulated vaccine against *F. tularensis*, allowing intradermal delivery and providing relatively high protective immunity with storage stability.

BRIEF DESCRIPTION OF THE DRAWINGS

The lyophilized stabilized formulation containing a live attenuated vaccine strain against tularemia is further described herein with reference to the accompanying drawings identified below.

DETAILED DESCRIPTION

The present invention starts with consideration of *F. novicida* (Fn), a closely related species to *Francisella tularensis* subsp. *tularensis* (Ftt), that is avirulent in humans. Namely, Fn with mutation iglD, the T6SS gene required for phagosome escape and intramacrophage replication (Fn-iglD) is configured to express the lipopolysaccharide (LPS) O-Antigen from FTT (Ftt(OAg$^{FTT}$). This is preferably achieved by removal of the entire OAg cluster consisting of 12 genes from Fn-iglD followed by the stepwise replacement of the OAg cluster consisting of 15 genes from Ft subsp. *holarctica* LVS strain which express OAg$^{FTT}$. The resultant strain, KKF768 (Fn-iglD OAg$^{FTT}$) expresses OAg$^{FTT}$ attached to its LPS.

For lyophilization of KKF768, a preferred stabilized formulation was employed that contained the stabilizer mix of 10.0% Trehalose (w/v), 5.0% Mannitol (w/v) and 0.2%

Cysteine (w/v), as cryoprotectants, hereinafter the mix is identified as "10% TMC." An aqueous solution of this stabilized mix was prepared that preferably contained a suspension of 1×10$^{10}$ cfu/mL of KKF768. Lyophilization then followed.

A preferred procedure of lyophilization is as follows. Fn-iglD OAg$^{FTT}$ is suspended in the 10% TMC solution is aliquoted (e.g., 0.5 ml) into 5.0 ml (20 mm×40 mm) vials with a fluoropolymer stopper (e.g., FLUROTEC® stopper) and then transferred to a LABCONCO® Freezone 12 L with a stoppering tray dryer attachment. Table 1 below provides the preferred range of parameters for lyophilzation used to provide the 10% TMC lyophilized formulation:

TABLE 1

Preferred Lyophilization Parameters

| Segment | | Shelf Temperature Setpoint (° C.) | Soak Time (hours) | Ramping Rate (° C./hour) | Pressure Setpoint (micron or PSIA) | Mbar |
|---|---|---|---|---|---|---|
| Load | Product Loading | 5.0 | 1.0 | | | |
| 1 | Freezing | −40.0 | 3.0 | 60.0[1] | | |
| 2 | Primary Drying | −30.0 | 48.0 | 30.0[2] | 40 micron | 0.52 |
| 3 | Secondary Drying | 5.0 | | 30.0[3] | | |
| 4 | Stoppering | 5.0 | | | 14.7 PSIA | No vacuum |

[1]The product is cooled to −40.0° C. from 5.0° C. at the preferred rate of 60.0° C. per hour or in the range of 55.0° C. per hour to 65.0° C. per hour.
[2]The frozen product at −40.0° C. is raised to −30.0° C. at the preferred rate of 30.0° C. per hour or in the range of 25.0° C. per hour to 35.0° C. per hour.
[3]The product at −30.0° C. is raised to 5.0° C. at the preferred rate of 30.0° C. per hour or in the range of 25.0° C. per hour to 35.0° C. per hour.

From the above, it can be appreciated that the freezing preferably occurs at a temperature range of −45.0° C. to −35.0° C. for a period of time in the range of 2.5 hours to 3.5 hours, primary drying occurs at a temperature of −35.0° C. to −25.0° C. at 0.45 Mbar to 0.55 Mbar for a time in the range of 40-55 hours, and secondary drying occurs at a temperature of 0° C. to 10° C., the chamber is then purged with nitrogen, and the sample can be stoppered in the vials and removed.

Viability of the lyophilized KK768 is initially summarized below in Table 2:

TABLE 2

Viability of KKF768 Lyophilized in 10% TMC and Stored at Various Temperatures and Times[1,2]

| Storage Condition | Week 1 | Week 2 | Week 4 | Week 8 | Week 12 | Week 24 |
|---|---|---|---|---|---|---|
| −20° C. | — | — | 9.62 | 9.35 | 9.33 | 9.42 |
| 4° C. | 9.59 | 9.47 | 9.10 | 8.58 | 8.1 | — |
| 25° C./60% RH | 8.95 | 7.29 | 6.96 | — | — | — |

[1]Pre-lyophilized 10.13; Post-lyophilized 9.74 (−0.39).
[2]Viability is reported in log$_{10}$ of colony forming units per vial. 0.5 mL of suspension lyophilized in each vial.

Figure 1:
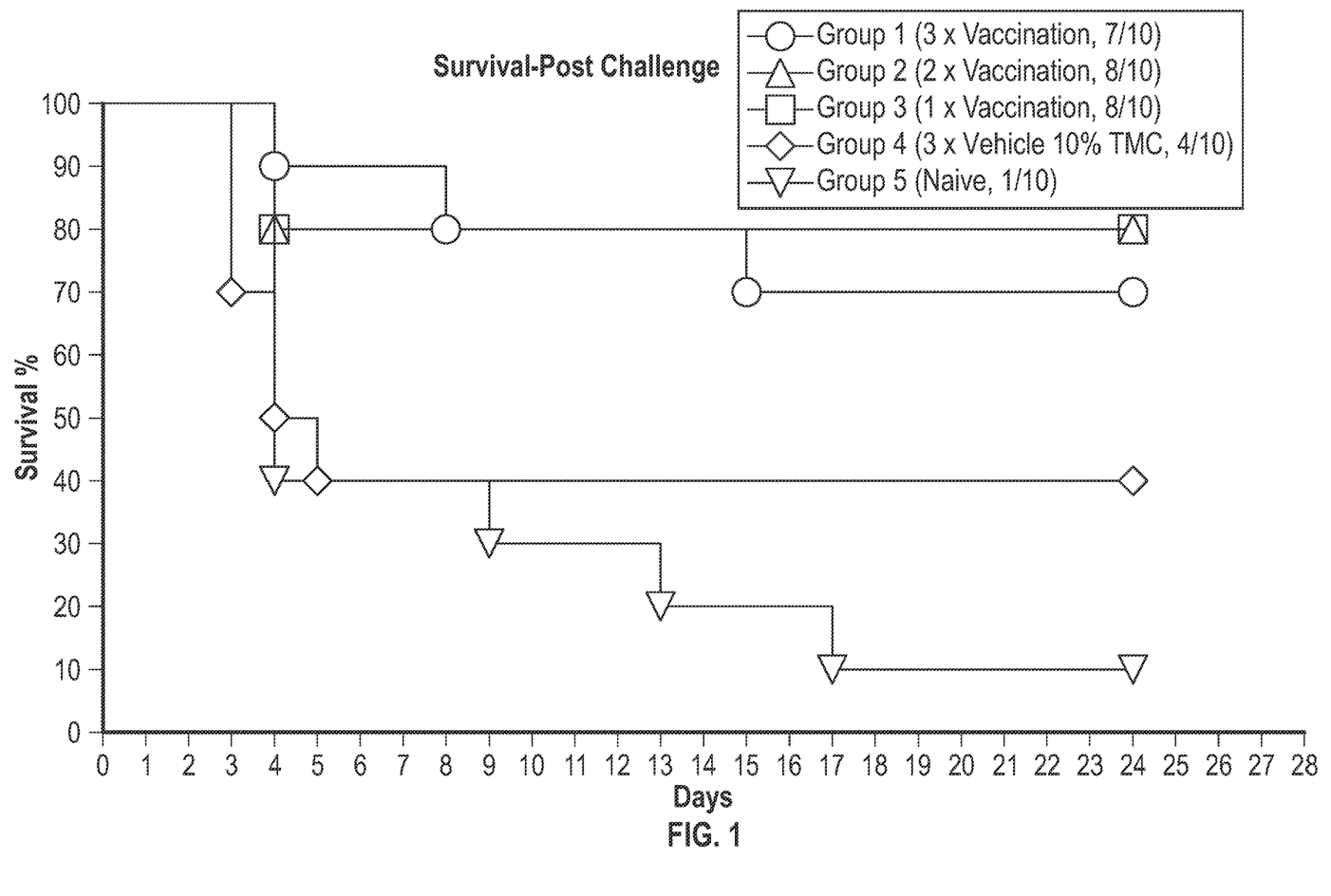
FIG. 1 illustrates the survival of F344 rats after intradermal administration of the 10% TMC stabilized lyophilized vaccine or vaccines and boosts upon challenge with a *F. tularensis* Schu S4 mutant strain by the intratracheal route.

FIG. 1 illustrates the survival of F344 rats after intradermal administration of the 10% TMC stabilized lyophilized vaccine or vaccines and boosts upon challenge with a *F. tularensis* Schu S4 mutant strain by the intratracheal route.

Correlates of immunity were next evaluated for the 10% TMC lyophilized KKF768 and as illustrated in the data below immune cells upregulated upon vaccination resulting in protective immunity after vaccination and boost.

Figure 2A:
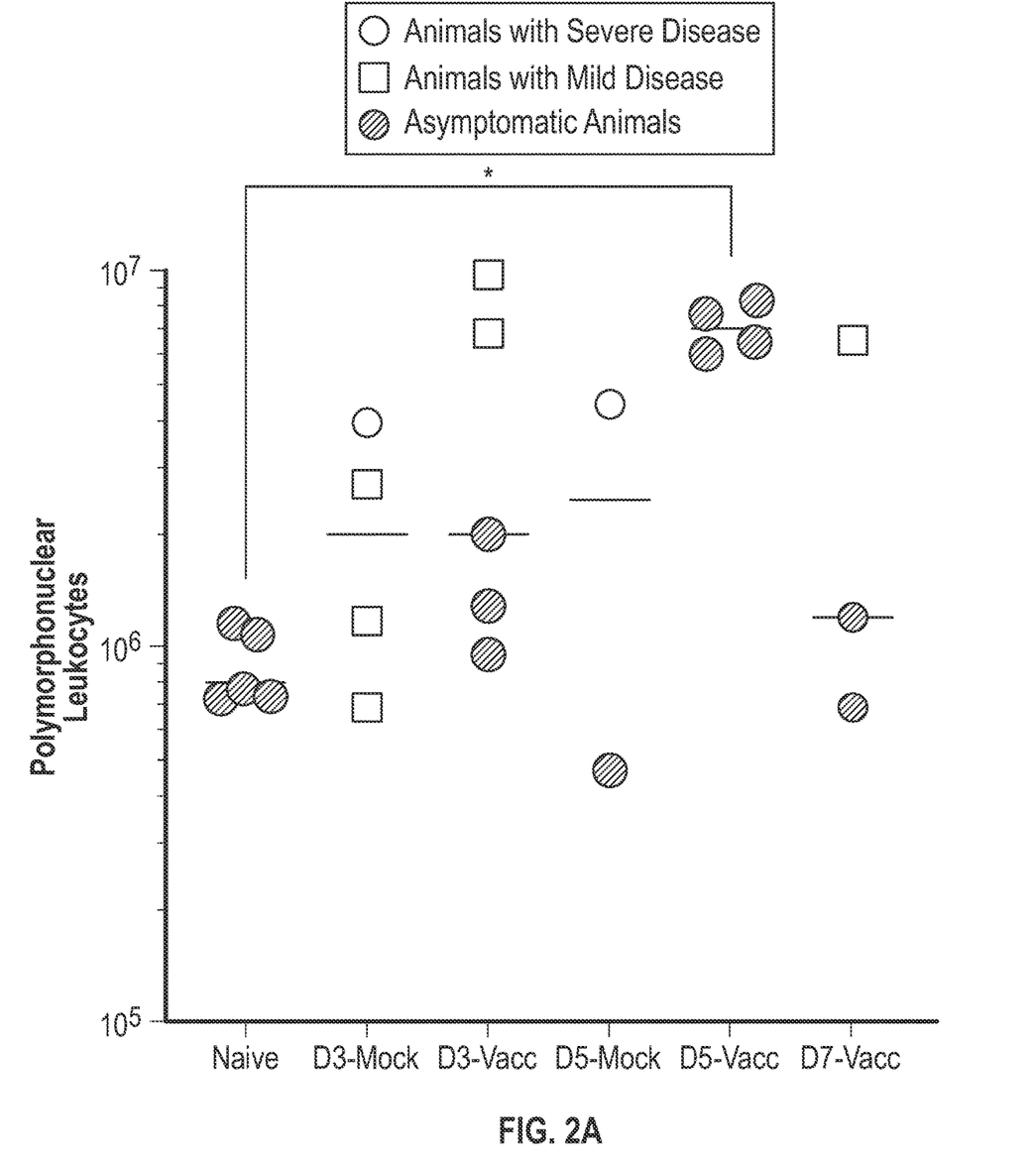
FIG. 2A plots the level of polymorphonuclear leukocytes populations in the lungs of 10% TMC lyophilized KKF768 and mock vaccinated rats at days 3, 5, and 7, following an intratracheal challenge with a potentially lethal dose of Ft SCHU S4.
Figure 2B:
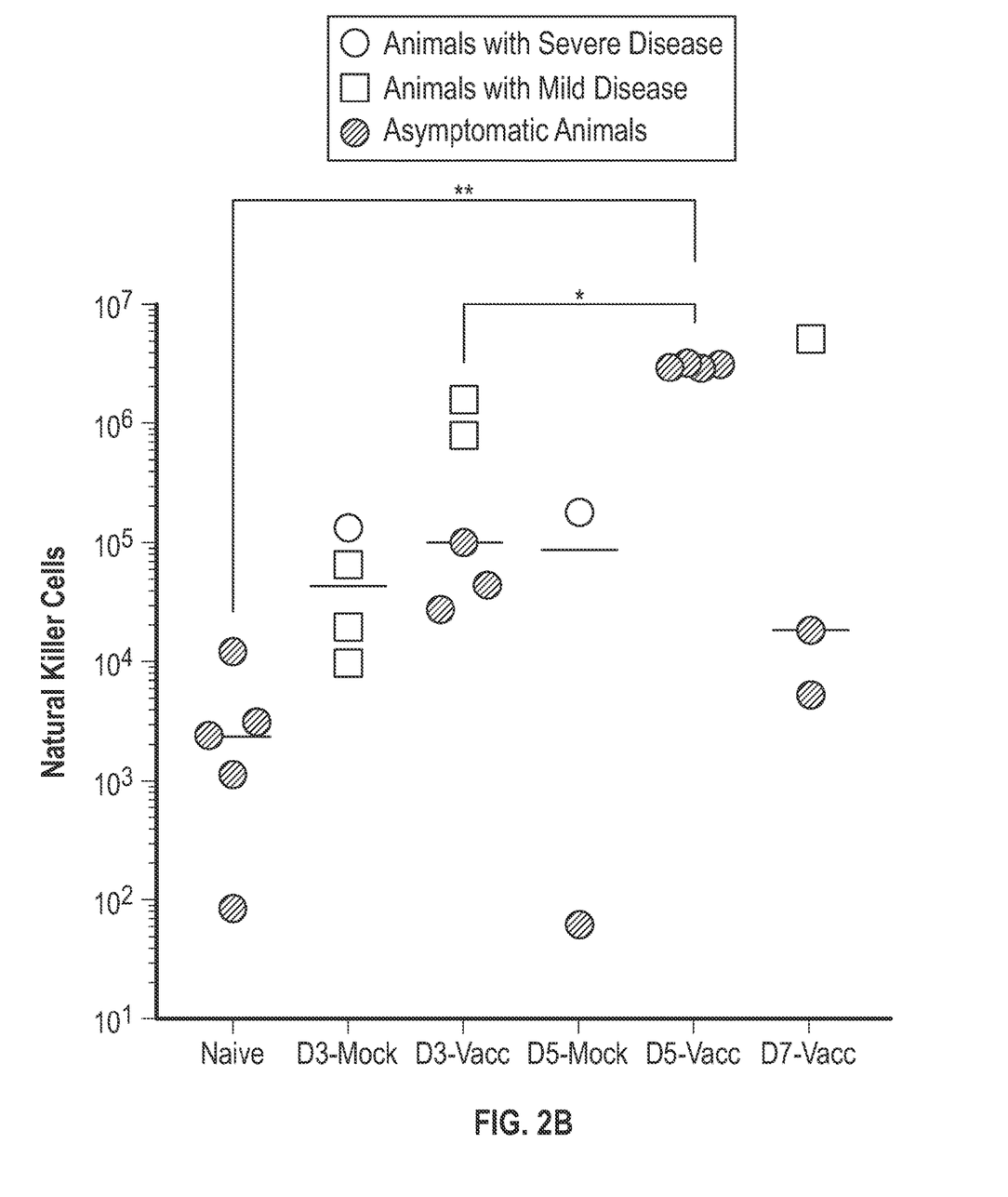
FIG. 2B plots the level of natural killer cell populations in the lungs of 10% TMC lyophilized KKF768 and mock vaccinated rats at days 3, 5, and 7, following an intratracheal challenge with a potentially lethal dose of Ft SCHU S4.
Figure 2C:
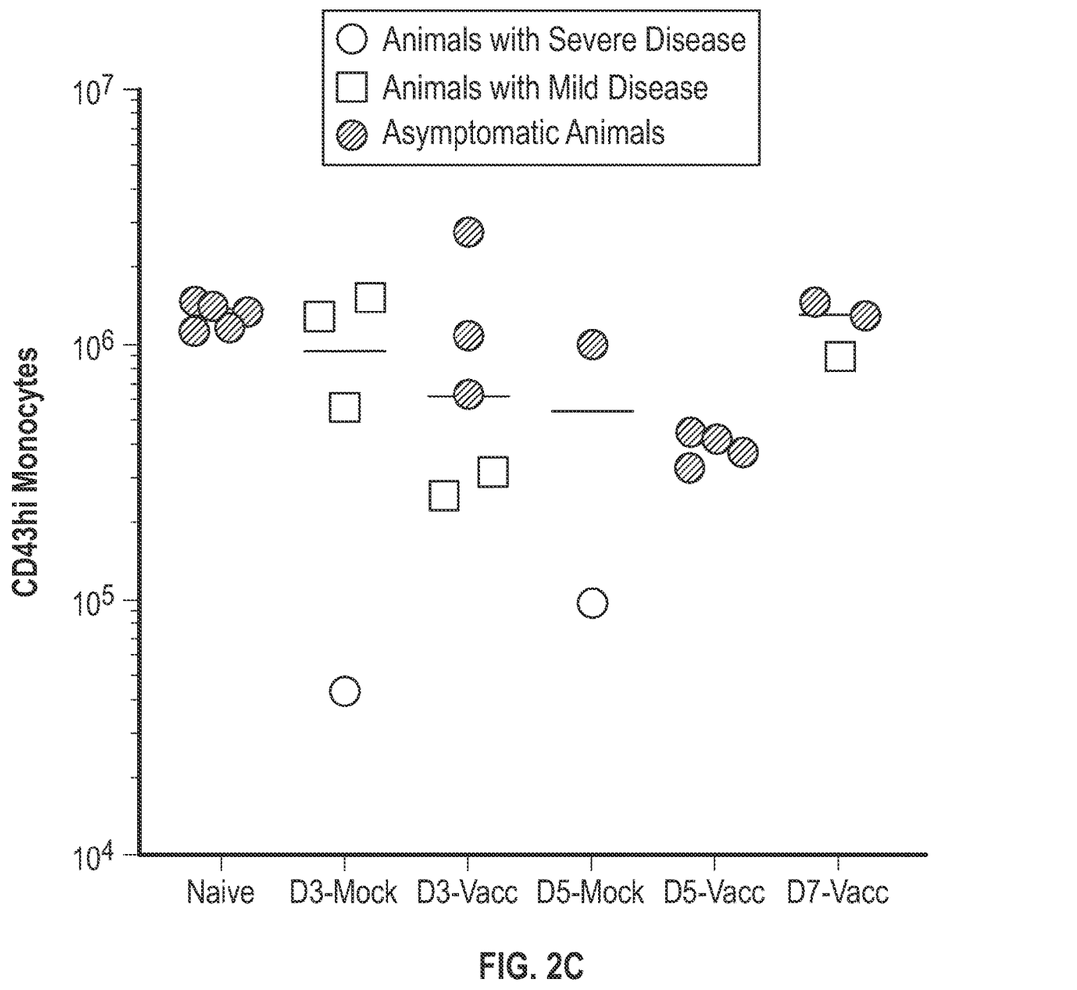
FIG. 2C plots the level of CD43hi monocytes in the lungs of 10% TMC lyophilized KKF768 and mock vaccinated rats at days 3, 5, and 7, following an intratracheal challenge with a potentially lethal dose of Ft SCHU S4.
Figure 2D:
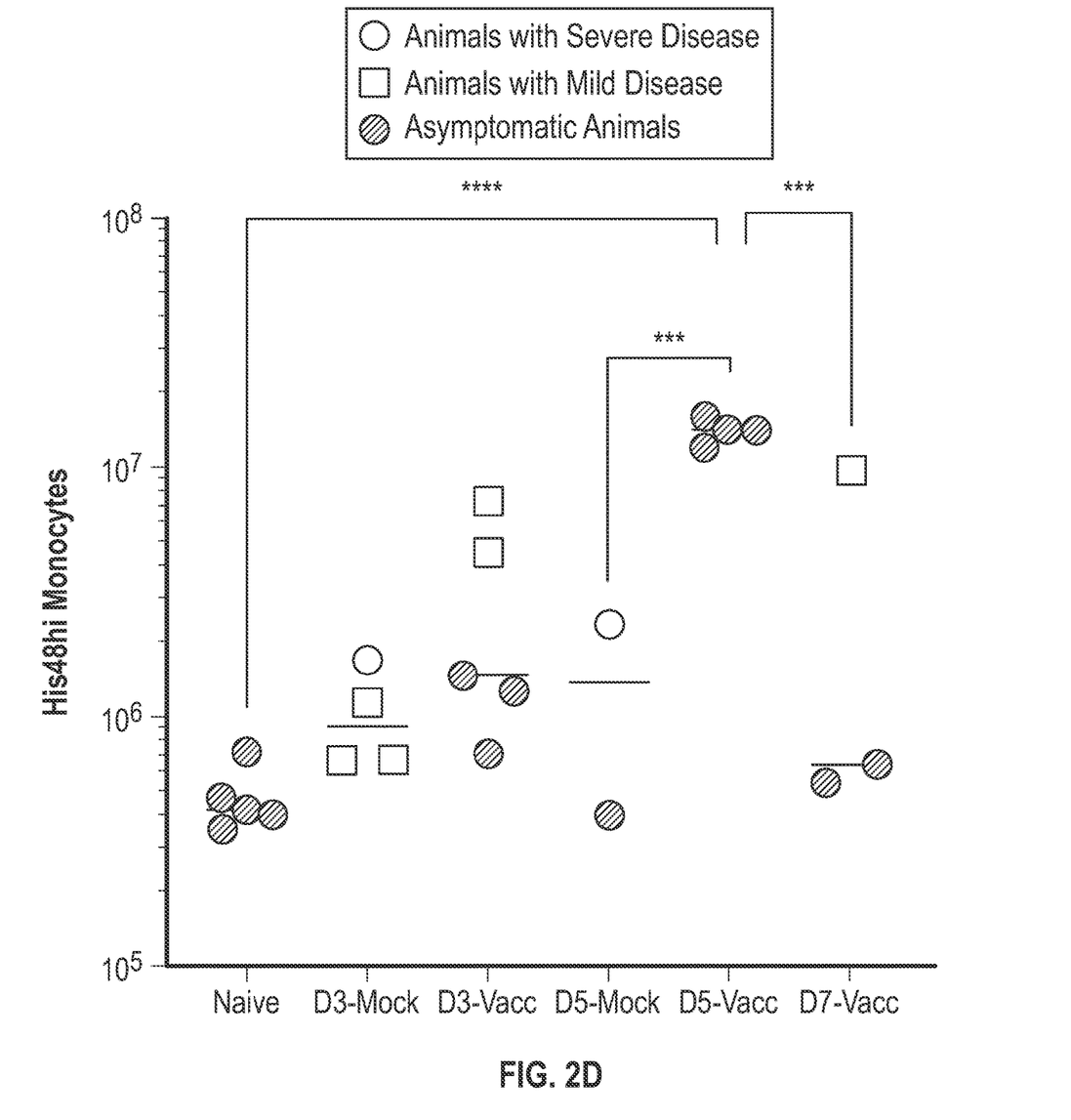
FIG. 2D plots the level of His48hi monocytes in the lungs of 10% TMC lyophilized KKF768 and mock vaccinated rats at days 3, 5, and 7, following an intratracheal challenge with a potentially lethal dose of Ft SCHU S4.

FIG. 2A plots the level of polymorphonuclear leukocytes populations in the lungs of 10% TMC lyophilized KKF768 and mock vaccinated rats at days 3, 5, and 7, following an intratracheal challenge with a potentially lethal dose of Ft SCHU S4. FIG. 2B plots the level of natural killer cell populations in the lungs of 10% TMC lyophilized KKF768 and mock vaccinated rats at days 3, 5, and 7, following an intratracheal challenge with a potentially lethal dose of Ft SCHU S4. FIG. 2C plots the level of CD43hi monocytes in the lungs of 10% TMC lyophilized KKF768 and mock vaccinated rats at days 3, 5, and 7, following an intratracheal challenge with a potentially lethal dose of Ft SCHU S4. FIG. 2D plots the level of His48hi monocytes in the lungs of 10% TMC lyophilized KKF768 and mock vaccinated rats at days 3, 5, and 7, following an intratracheal challenge with a potentially lethal dose of Ft SCHU S4.

Figure 3A:
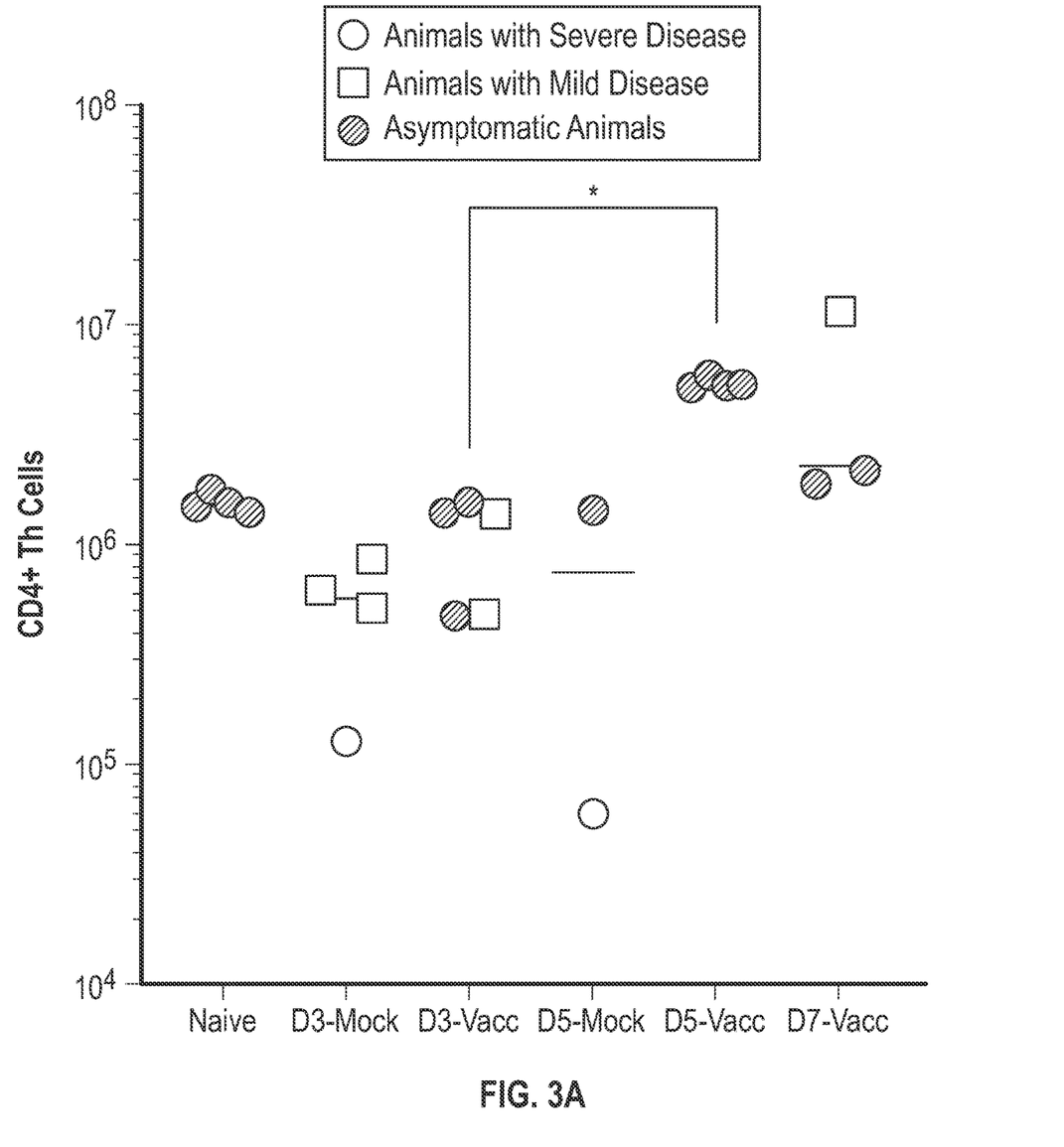
FIG. 3A plots the level of CD4+Th cells in the lungs of 10% TMC lyophilized KK768 and mock vaccinated rats at days 3, 5, and 7 following an intratracheal challenge with a potentially lethal does of Ft SCHU S4.
Figure 3B:
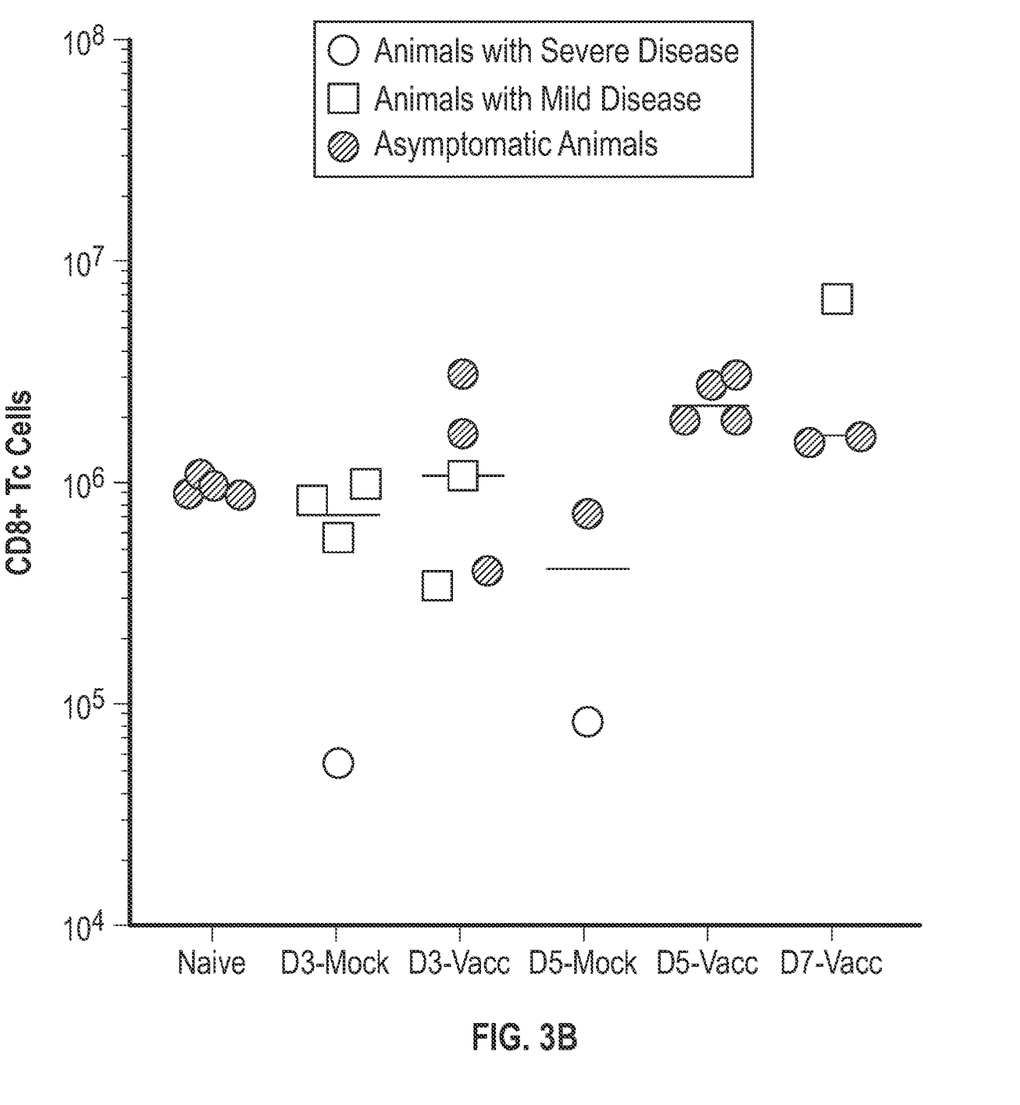
FIG. 3B plots the level of CD8+Tc cells in the lungs of 10% TMC lyophilized KK768 and mock vaccinated rats at days 3, 5, and 7 following an intratracheal challenge with a potentially lethal dose of Ft SCHU S4.
Figure 3C:
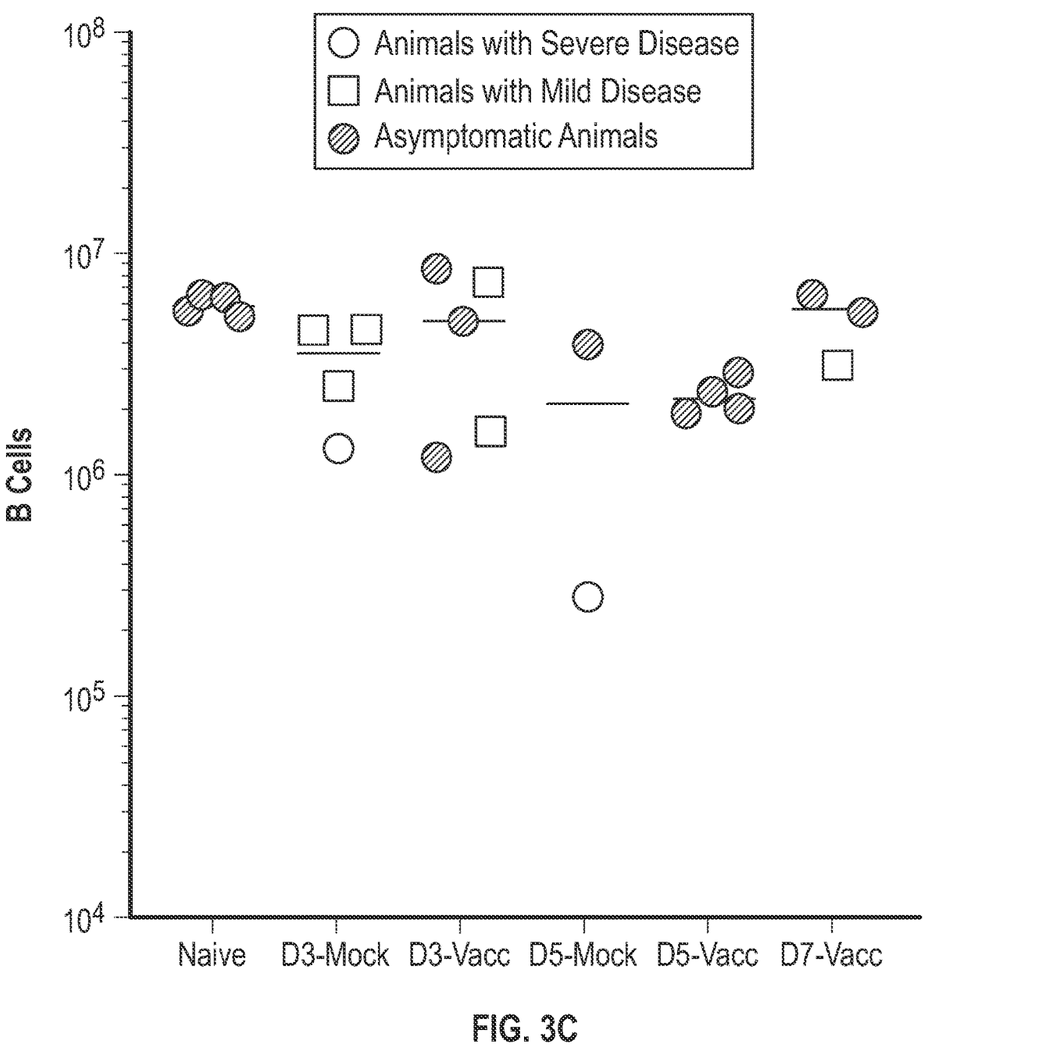
FIG. 3C plots the level of B cells in the lungs of 10% TMC lyophilized KK768 and mock vaccinated rats at days 3, 5, and 7 following an intratracheal challenge with a potentially lethal dose of Ft SCHU S4.

FIG. 3A plots the level of CD4+Th cells in the lungs of 10% TMC lyophilized KK768 and mock vaccinated rats at days 3, 5, and 7 following an intratracheal challenge with a potentially lethal does of Ft SCHU S4. FIG. 3B plots the level of CD8+Tc cells in the lungs of 10% TMC lyophilized KK768 and mock vaccinated rats at days 3, 5, and 7 following an intratracheal challenge with a potentially lethal dose of Ft SCHU S4. FIG. 3C plots the level of B cells in the lungs of 10% TMC lyophilized KK768 and mock vaccinated rats at days 3, 5, and 7 following an intratracheal challenge with a potentially lethal dose of Ft SCHU S4.

Figure 4A:
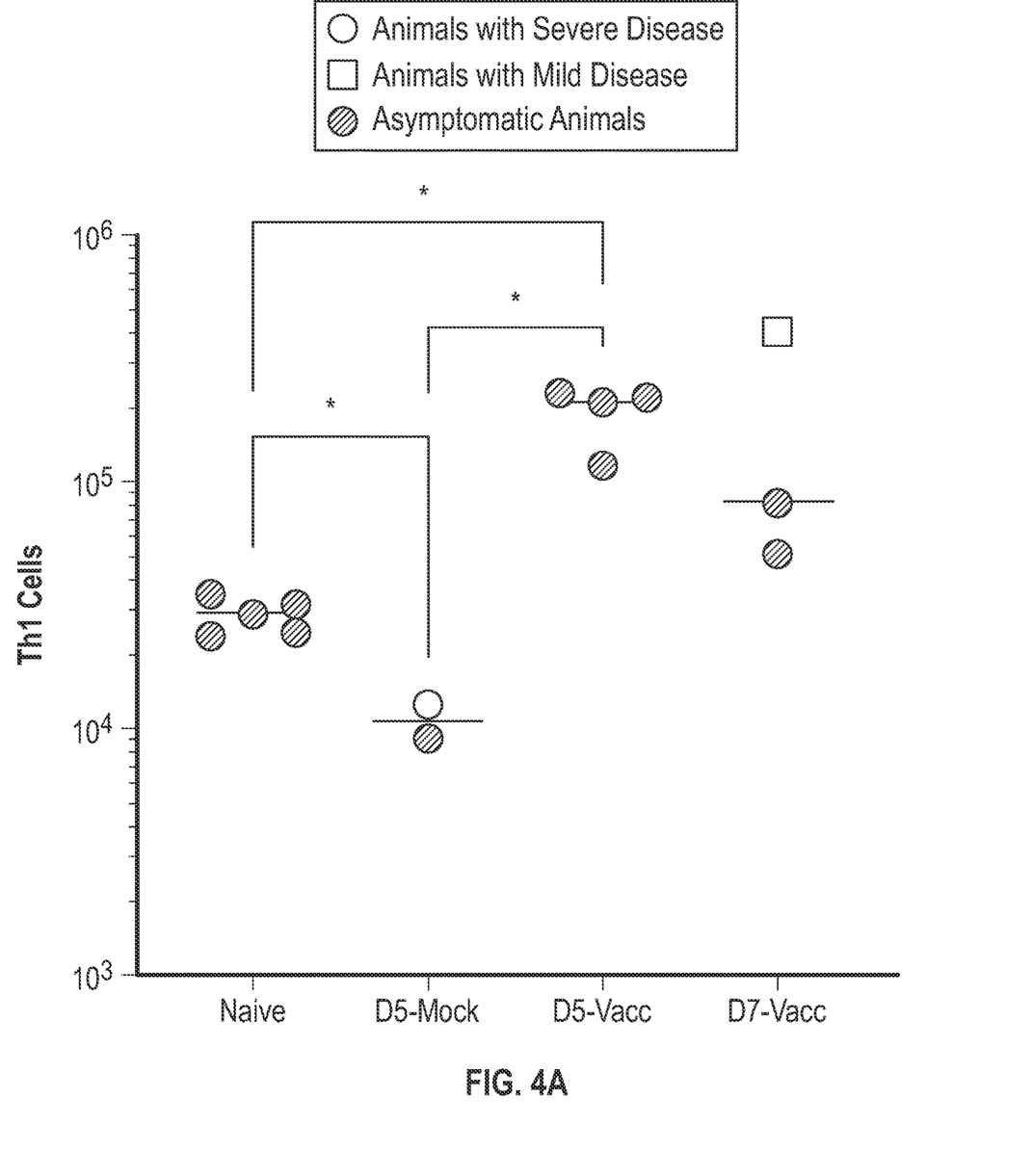
FIG. 4A plots the level of Th1 cells in the lungs of 10% TMC lyophilized KKF768 and mock vaccinated rats at days 3, 5, and 7 following an intratracheal challenge with a potentially lethal dose of Ft SCHU S4.
Figure 4B:
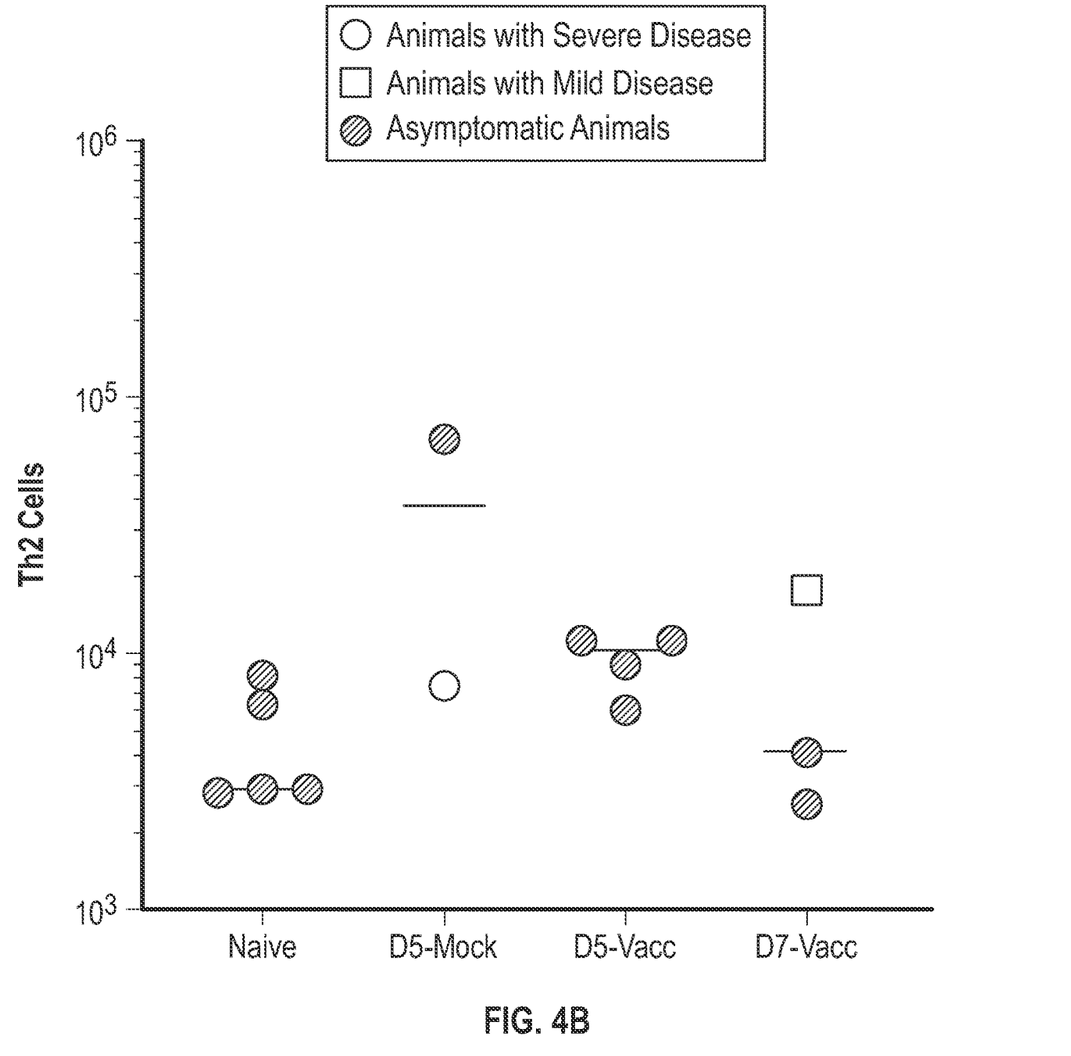
FIG. 4B plots the level of Th2 cells in the lungs of 10% TMC lyophilized KKF768 and mock vaccinated rats at days 3, 5, and 7 following an intratracheal challenge with a potentially lethal dose of Ft SCHU S4. F FIG. 4C plots the level of T171 cells in the lungs of 10% TMC lyophilized KKF768 and mock vaccinated rats at days 3, 5, and 7 following an intratracheal challenge with a potentially lethal dose of Ft SCHU S4.
Figure 4C:
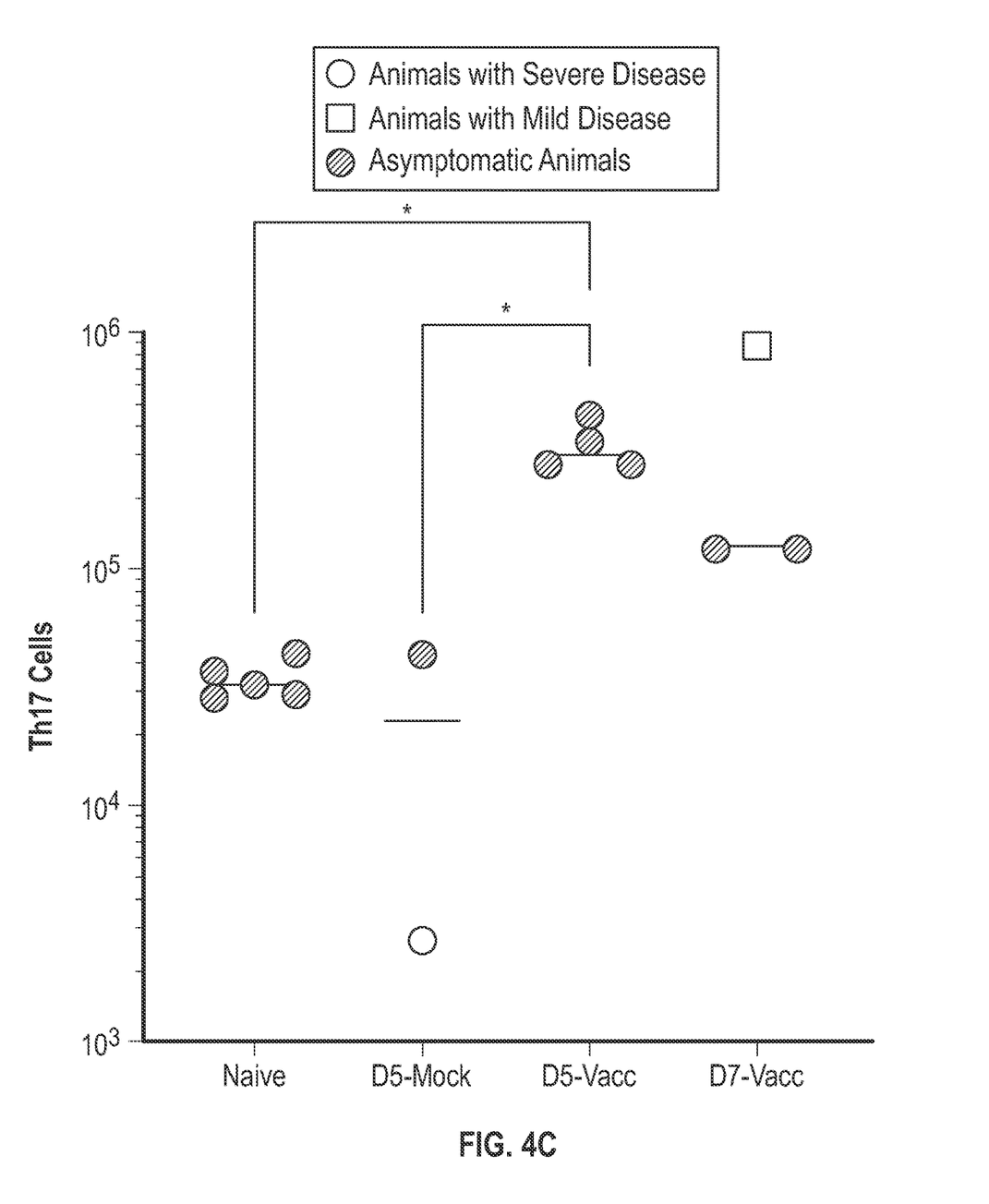
Figure 4D:
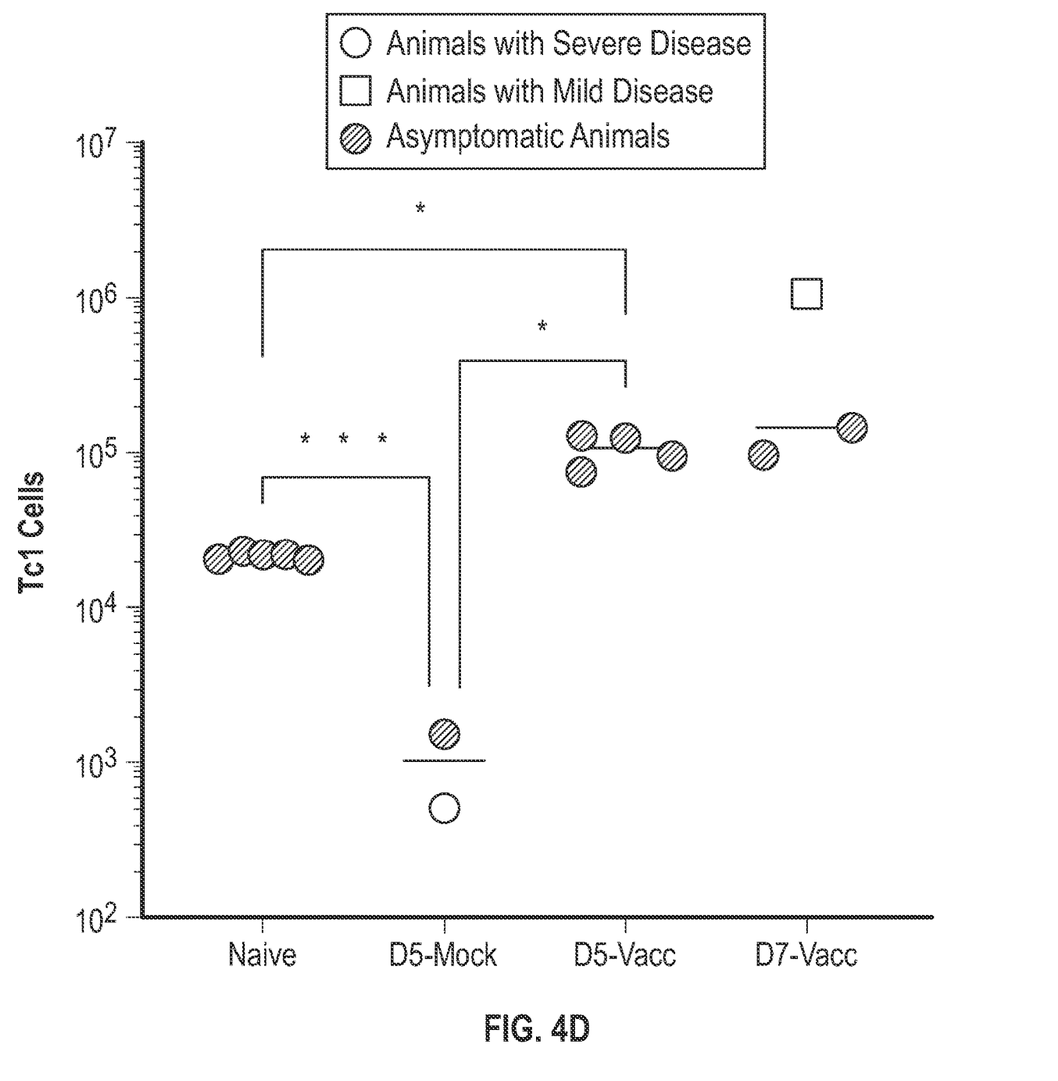
FIG. 4D plots the level of Tc1 cells in the lungs of 10% TMC lyophilized KKF768 and mock vaccinated rats at days 3, 5, and 7 following an intratracheal challenge with a potentially lethal dose of Ft SCHU S4.
Figure 4E:
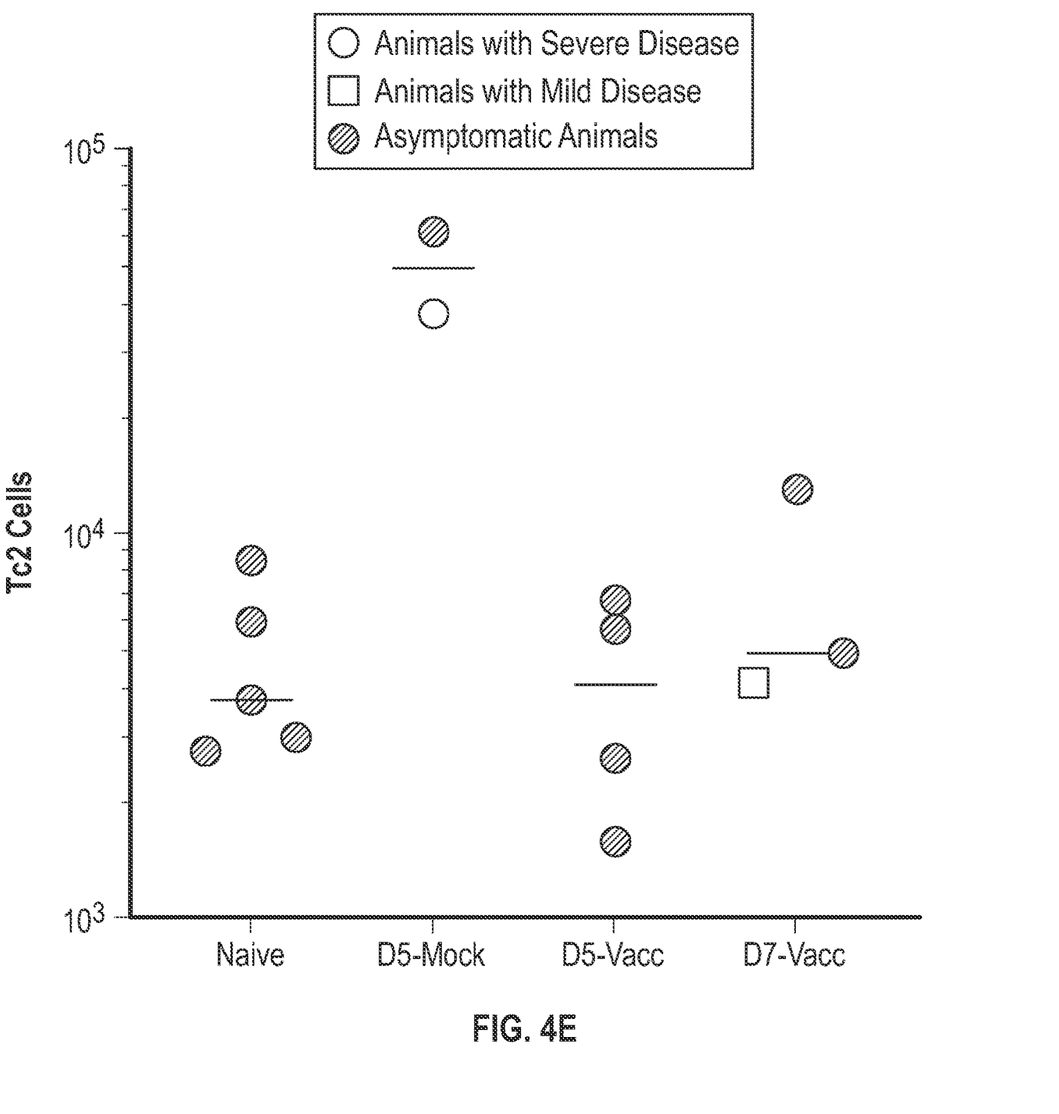
FIG. 4E plots the level of Tc2 cells in the lungs of 10% TMC lyophilized KKF768 and mock vaccinated rats at days 3, 5, and 7 following an intratracheal challenge with a potentially lethal dose of Ft SCHU S4.

FIG. 4A plots the level of Th1 cells in the lungs of 10% TMC lyophilized KK768 and mock vaccinated rats at days 3, 5, and 7 following an intratracheal challenge with a potentially lethal dose of Ft SCHU S4. FIG. 4B plots the level of Th2 cells in the lungs of 10% TMC lyophilized KK768 and mock vaccinated rats at days 3, 5, and 7 following an intratracheal challenge with a potentially lethal dose of Ft SCHU S4. FIG. 4C plots the level of T171 cells in the lungs of 10% TMC lyophilized KK768 and mock vaccinated rats at days 3, 5, and 7 following an intratracheal challenge with a potentially lethal dose of Ft SCHU S4. FIG. 4D plots the level of Tc1 cells in the lungs of 10% TMC lyophilized KK768 and mock vaccinated rats at days 3, 5, and 7 following an intratracheal challenge with a potentially lethal dose of Ft SCHU S4. FIG. 4E plots the level of Tc2 cells in the lungs of 10% TMC lyophilized KKF768 and mock vaccinated rats at days 3, 5, and 7 following an intratracheal challenge with a potentially lethal dose of Ft SCHU S4. FIG.

Figure 4F:
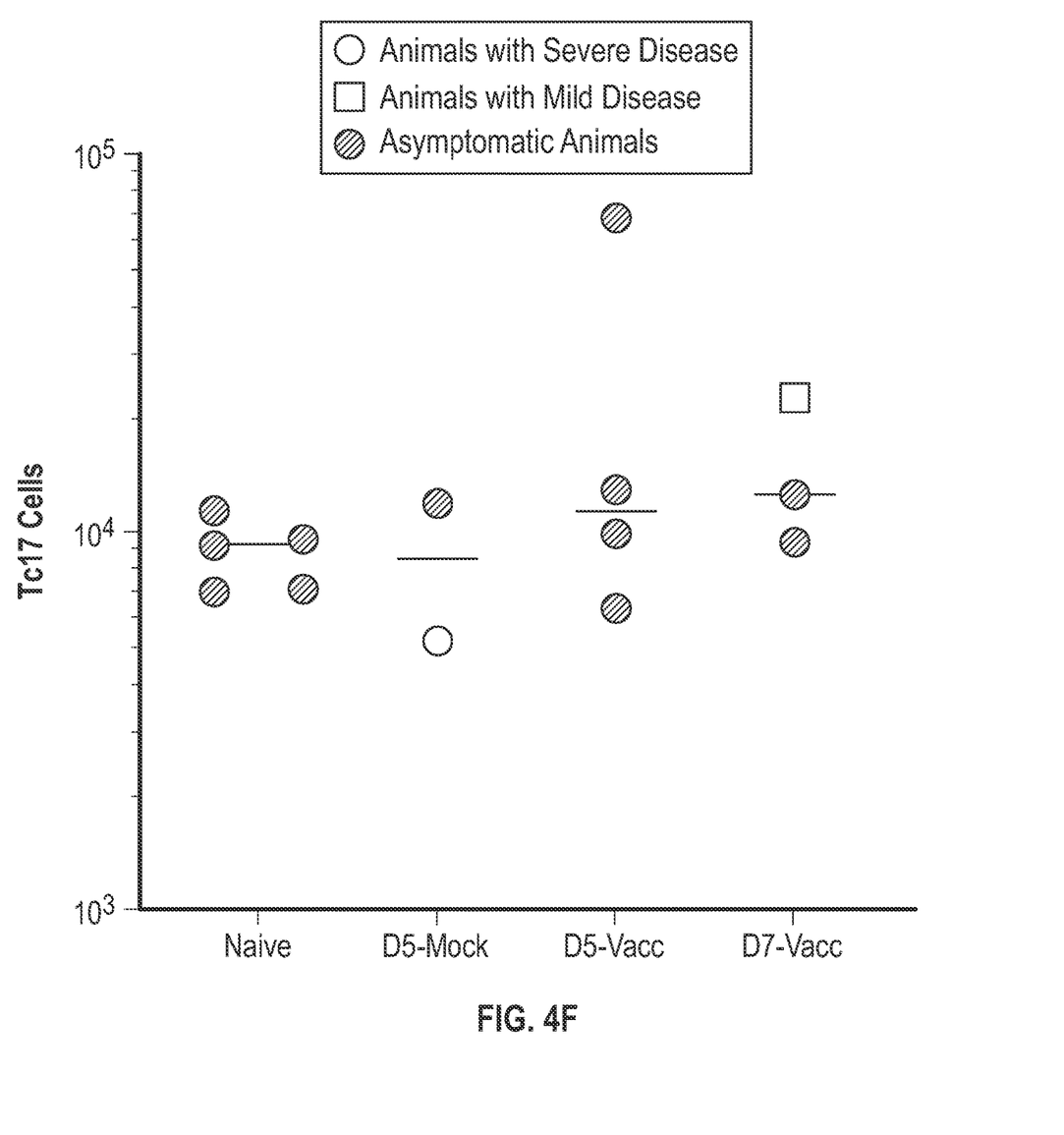
FIG. 4F plots the level of Tc17 cells in the lungs of 10% TMC lyophilized KKF768 and mock vaccinated rats at days 3, 5, and 7 following an intratracheal challenge with a potentially lethal dose of Ft SCHU S4.

4F plots the level of Tc17 cells in the lungs of 10% TMC lyophilized KK768 and mock vaccinated rats at days 3, 5, and 7 following an intratracheal challenge with a potentially lethal dose of Ft SCHU S4.

As may now be appreciated from the above, the present disclosure stands directed to an immunogenic agent for use in the prevention or treatment of infection by *Francisella tularensis* in an animal, the immunogenic agent comprising a lyophilized and stabilized formulation of Fn-iglD OAg$^{FTT}$. The animal may be a human. A pharmaceutical composition may also be provided containing the lyophilized stabilized formulation of Fn-iglD OAg$^{FTT}$. In process form, the present disclosure provides a method of producing an immunogenic agent for use in the prevention or treatment of infection by *Francisella tularensis* in an animal comprising the steps of supplying the immunogenic agent comprising Fn-iglD OAg$^{FTT}$ and subjecting said immunogenic agent to lyophilization and recovering a lyophilized and stabilized form of said immunogenic agent. The present disclosure also relates to a method of treatment of an animal in need of treatment for prevention or infection by *Francisella tularensis* comprising administration of the immunogenic agent comprising the lyophilized stabilized formulation of Fn-iglD OAg$^{FTT}$.

What is claimed is:

1. A method of producing an immunogenic agent for use in the prevention or treatment of infection by *Francisella tularensis* in an animal comprising the steps of:
   supplying the immunogenic agent comprising Fn-iglD OAg$^{FTT}$ in a stabilizer mix of 10.0% Trehalose (w/v), 5.0% Mannitol (w/v) and 0.2% Cysteine (w/v) as cryprotecatants;
   subjecting said immunogenic agent to lyophilization and recovering a lyophilized and stabilized form of said immunogenic agent
   wherein said lyophilization comprises providing said immunogenic agent at 5.0° C. and freezing said immunogenic agent to a temperature of −45.0° C. to −35.0° C. at a cooling rate of 55.0° C. per hour to 65° C. per hour and maintaining said temperature of −45° C. to −35° C. for a period of time in the range of 2.5 hours to 3.5 hours;
   primary drying at a temperature of −35.0° C. to −25.0° C. at 0.45 mbar to 0.55 mbar for a time in the range of 40-55 hours; and
   raising said primary drying temperature to a secondary drying at a temperature of 0° C. to 10° C. at a rate of 25° C. to 35° C. per hour immediately followed by purging with nitrogen wherein said immunogenic agent is then placed in a vial and stoppered.

* * * * *